(12) United States Patent
Marini et al.

(10) Patent No.: US 11,517,547 B2
(45) Date of Patent: Dec. 6, 2022

(54) COMBINATION THERAPY TO TREAT UREA CYCLE DISORDERS

(71) Applicant: Baylor College of Medicine, Houston, TX (US)

(72) Inventors: Juan C. Marini, Houston, TX (US); Sandesh Chakravarthy Sreenath Nagamani, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/624,834

(22) PCT Filed: Jun. 28, 2018

(86) PCT No.: PCT/US2018/040088
§ 371 (c)(1),
(2) Date: Dec. 19, 2019

(87) PCT Pub. No.: WO2019/006164
PCT Pub. Date: Jan. 3, 2019

(65) Prior Publication Data
US 2020/0170984 A1    Jun. 4, 2020

Related U.S. Application Data

(60) Provisional application No. 62/526,054, filed on Jun. 28, 2017.

(51) Int. Cl.
| | |
|---|---|
| *A61K 31/192* | (2006.01) |
| *A61K 31/216* | (2006.01) |
| *C12Q 1/6869* | (2018.01) |
| *A61K 9/00* | (2006.01) |
| *A61K 45/06* | (2006.01) |

(52) U.S. Cl.
CPC .......... *A61K 31/192* (2013.01); *A61K 31/216* (2013.01); *C12Q 1/6869* (2013.01); *A61K 9/0053* (2013.01); *A61K 45/06* (2013.01)

(58) Field of Classification Search
CPC .. A61K 31/192; A61K 31/216; A61K 9/0053; A61K 45/06; C12Q 1/6869
USPC ....................................................... 514/533
See application file for complete search history.

(56) References Cited

U.S. PATENT DOCUMENTS

| | | |
|---|---|---|
| 5,434,166 A | 7/1995 | Glasebrook |
| 6,362,226 B2 | 3/2002 | Phillips, III et al. |
| 6,503,530 B1 | 1/2003 | Kang et al. |
| 7,396,659 B2 | 7/2008 | Singh |
| 9,078,865 B2 | 7/2015 | Lee |
| 9,737,499 B2 | 8/2017 | Lee |
| 10,092,532 B2 | 10/2018 | Lee |
| 2002/0115716 A1 | 8/2002 | Chaturvedi et al. |
| 2007/0004805 A1 | 1/2007 | Jobdevairakkam et al. |
| 2010/0008859 A1 | 1/2010 | Scharschmidt |
| 2020/0147016 A1 | 5/2020 | Lee |

FOREIGN PATENT DOCUMENTS

| | | |
|---|---|---|
| WO | 2007005633 A2 | 1/2007 |
| WO | 2008083226 A2 | 7/2008 |
| WO | 2010/025303 A1 | 3/2010 |

OTHER PUBLICATIONS

Maestri et al., Long-Term Treatmentof Girls with Ornithine Transcarbamylase Deficiency, The New England Journal of Medicine, 1996, vol. 335, No. 12, 855-859 (Year: 1996).*
Häberle et al.: "Suggested guidelines for the diagnosis and management of urea cycle disorders", Orphanet Journal of Rare Diseases, vol. 7, No. 1, May 29, 2012 (May 29, 2012), p. 32, Biomed Central Ltd, Lo.
Martin-Hernandez et al.: "Urea cycle disorders in Spain: an observational, cross-sectional and multicentric study of 104 cases", Orphanet Journal of Rare Diseases, vol. 9, No. I, Nov. 30, 2014 (Nov. 30, 2014), p. 187, Biomed Central Ltd, Lo.
Nagamani et al.: "A randomized trial to study the comparative efficacy of phenylbutyrate and benzoate on nitrogen excretion and ureagenesis in healthy volunteers", Genetics in Medicine, vol. 20, No. 7, Oct. 12, 2017 (Oct. 12, 2017), pp. 708-716, Williams and Wilkins, Baltimore, MD, US.
Rxlist. "Ammonul" Mar. 23, 2016 (Mar. 23, 2016) <https://www.rxlist.com/ammonul-drug.htm#description>; p. 1, para 2, 5, p. 2, para 1, table 1, p. 3, para 4-6, p. 7.
Marini et al. "Phenylbutyrate improves nitrogen disposal via an alternative pathway without eliciting an increase in protein breakdown and catabolism in control and ornithine transcarbamylase-deficient patients" The American Journal of Clinical Nutrition. Apr. 13, 2011 (Apr. 13, 2011) vol. 6, p. 1248-1254; p. 1248.
Upadhyay et al. "Hyperammonemia: What Urea-lly Need to Know: Case Report of Severe Noncirrhotic Hyperammonemic Encephalopathy and Review of the Literature" Case Reports in Medicine. Sep. 21, 2016 (Sep. 21, 2016) vol. 2016, p. 1-10; p. 5.
Machado et al. "Hyperammonemia due to urea cycle disorders: a potentially fatal condition in the intensive care setting" Journal of Intensive Care. Mar. 13, 2014 (Mar. 13, 2014) vol. 2, p. 1-5; p. 4.
"Ammo naps-sodium phenylbutyrate. EPAR summary for the public," website of European Medicines Agency (EMEA), located at www.ema.europa.eu/docs/en_ GB/document_library/EPAR -_Summary _for_ the public/human /000219/WC500024 751.pdf, last updated in Dec. 2009.
"Buphenyl (sodium phenylbutyrate) Tablets I Buphenyl (sodium phenylbutyrate) Powder," Patient Package Insert, Ucyclyd Pharma, Inc., Apr. 2009.
"Scientific Discussion," module reflecting the initial scientific discussion for the approval of Ammonpas, updated until Nov. 1, 2001, European Medicines Agency, pp. 1-12, 2005.

(Continued)

*Primary Examiner* — Kristin A Vajda
(74) *Attorney, Agent, or Firm* — Norton Rose Fulbright US LLP

(57) ABSTRACT

Embodiments of the disclosure include certain formulations for methods of treating urea cycle disorders. The methods encompass compositions that comprise benzoate and phenylbutyrate that may be at certain doses and have certain ratios of the components. The benzoate and phenylbutyrate may act synergistically in treatment of the urea cycle disorders, in particular embodiments.

12 Claims, 5 Drawing Sheets

(56) References Cited

OTHER PUBLICATIONS

Amaral et al.; "a-Ketoisocaproic acid and leucine provoke mitochondrial bioenergetic dysfunction in rat brain", Science Direct—Brain Research 1324 75-84 (2010).
Bunchman et al., "Phenylacetate and Benzoate Clearance in a Hyperammonemic Infant on Sequential Hemodialysis and Hemofiltration", Pediatric Nephrology 200707 DE, vol. 22, No. 7, Jul. 2007, pp. 1062-1065.
Darmaun et al., Am. J. Physiol, 1998;274(5):E801-807.
Fisher et al., "Molecular phenotypes in cultured maple syrup urine disease cells: Complete E1a eDNA sequence and mRNA and subunit contents of the human branched chain a-keto acid dehydrogenase complex," The Journal of Biological Chemistry, 264(6):3448-3453, 1989.
Funchal et al., "Morphological alterations and induction of oxidative stress in glial cells caused by the branched-chain a-keto acids accumulting in maple syrup urine disease", Neurochemistry International 49 640-650 (2006).
Funchal et al., "Evidence That the Branched-Chain a-Keto Acids Accumulating in Maple Syrup Urin Diease Induce Morpholigical Alteration and Death in Cultured Astroxytes from Rat Ceberal Cortex", GLIA 48:230-240 (2004).
Le Bacquer et al., "Acute depletion of plasma glutamine increases leucine oxidation in prednisone-treated humans," Clin Nutr., 26(2):231-238, 2007.
Leandro etal., "Protein misfolding in conformational disorders: rescue of folding defects and chemical chaperoning," Mini Reviews in Medicinal Chemistry, 8:901-911, 2008.
McKeon, "MSUD Research Update," MSUD Newsletter, Maple Symp Urine Disease Family Support Group, vol. 23, No. 1, pp. 1 and 13, 2006.
Package Leaflet: Information for the User-Ammonaps 940 mg/g granules-sodium phenylbutyrate, website of the electronic Medicines Compendium (eMC), located at www.medicines.org.uk/emc/medicine/24885/PIL/ammonaps%20940%20mg~g%20granules/, pp. 1-5, last approved in Oct. 2010.
Riazi et al., Am J Physiol Endocrinol Metab, 2004;287:E142-E149.
Scaglia et al., "Clinical consequences of urea cycle enzyme deficiencies and potential links to arginine and nitric oxide metabolism," J Nutr, 134(10 Suppl):2775S-2782S; discussion 2796S-2797S, 2004.
Scaglia et al., "Effect of Alternative Pathway Therapy on Branched Chain Amino Acid Metabolism in Urea Cycle Disorder Patients", Molecular Genetics and Metabolism, Apr. 2004, vol. 81, No. Suppl 1, pp. S79-S85.
Schwartz et al., "Treatment of inborn em,>rs of metabolism," J Pediatr (Rio J), 84(4 Suppl):S8-19, 2008.
Self et al., "Glutamine Synthesis in the Developing Porcine Placenta", Biology of Reproduction 70, 144-1451 (2004).
Toshima et al., "Activation ofbranched-chain alpha-ketoacid dehydrogenase complex by alpha-chloroisocaproate in normal and enzyme-deficient fibroblasts," Clin Chim Acta, 147(2): 103-108, 1985.
Zhao et al., "Site-directed mutagenesis of phosphorylation sites of the branched chain a-ketoacid dehydrogenase complex," The Journal of Biological Chemistry, 269(28): 18583-18587, 1994.
Husson et al: "Efficacy and safety of i.v. sodium benzoate in urea cycle disorders: a multicentre retrospective study", Orphanet J. Rare Dis., vol. 11, No. 1, p. 1-8. 2016.

* cited by examiner

COMBINATION THERAPY TO TREAT UREA CYCLE DISORDERS

CROSS-REFERENCE TO RELATED APPLICATIONS

This application is a national phase application under 35 U.S.C. § 371 that claims priority to International Application No. PCT/US2018/040088 filed Jun. 28, 2018, which claims priority to U.S. Provisional Patent Application Ser. No. 62/526,054, filed on Jun. 28, 2017, both of which are incorporated by reference herein in their entirety.

STATEMENT REGARDING FEDERALLY SPONSORED RESEARCH OR DEVELOPMENT

This invention was made with government support under cooperative agreement 58-3092-5-001 and R03 HD078447, respectively awarded by USDA—Agricultural Research Service and National Institutes of Research Resources. The government has certain rights in the invention.

TECHNICAL FIELD

Embodiments of the disclosure include at least the fields of cell biology, molecular biology, physiology, and medicine.

BACKGROUND

Urea cycle is the main pathway in humans for the disposal of waste-nitrogen derived from the breakdown of dietary and endogenous proteins. The urea cycle comprising five catalytic enzymes (CPS1; OTC; ASS1; ASL; and ARG1), a cofactor synthesizing enzyme (NAGS), and two transporters (SLC25A15 and SLC25A13) facilitates the transfer of waste nitrogen from ammonia and aspartate to urea (FIG. 2). Deficiency of one of these enzymes or transporters causes urea cycle disorders (UCDs), a group of inborn errors of metabolism characterized by a decreased ability to dispose nitrogen and accumulation of ammonia (hyperammonemia) in tissues and blood (Brusilow and Horwich, 2009). Hyperammonemia can have serious consequences, and if severe, can result in intellectual disability, neurocognitive deficits, and even coma and death (Msall et al., 1984; Maestri et al., 1999). Thus, the main focus of treatment for UCDs is the prevention and treatment of hyperammonemia.

Nitrogen-scavenging medications, which use alternative pathways to dispose nitrogen, have become a standard-of-care for the prevention and treatment of hyperammonemia in UCDs (Ah Mew et al., 1993; Batshaw et al., 2001). For long-term management, oral formulations of benzoate and phenylbutyrate are the commonly used alternative pathway therapies. Benzoate combines with glycine to form hippuric acid (HA). Phenylbutyrate, a prodrug, is converted to phenylacetate (PAA) by β-oxidation; PAA conjugates with glutamine to form phenylacetylglutamine (PAGN) (FIG. 3). Because glutamine has two nitrogen atoms compared to one in glycine, at least in theory, on a mole-per-mole basis the nitrogen-scavenging efficacy of phenylbutyrate should be twice that of benzoate. However, in vivo efficacy is dependent on medication absorption, conversion into active metabolite, and the efficacy of conjugation with amino acids. The conversion of benzoate into HA has been estimated to range from 65% to virtually 100% (Mitch and Brusilow, 1982; Simell et al., 1986). Similarly, the conversion of phenylbutyrate to PAGN ranges from 50% to over 90% (Simell et al., 1986; Lee et al., 2010). It is thus not known whether the nitrogen-scavenging efficacy of phenylbutyrate is indeed better than benzoate.

To date, the comparative in vivo efficacy of phenylbutyrate and benzoate on nitrogen excretion in humans has not been systematically studied. In fact, detailed pharmacokinetic studies of either medication in individuals with UCDs were lacking until basic kinetic studies were performed with sodium phenylbutyrate (Lee et al., 2010). Moreover, even preclinical data are lacking as nonprimates conjugate glycine with phenylacetate and are hence not useful models to assess nitrogen-scavenging capacity of these medications (James et al., 1972; Jones, 1982). In spite of the lack of evidence, the theoretical advantage of phenylbutyrate over benzoate is likely one of the reasons for the preferential use of phenylbutyrate in the United States. This approach increases the economic burden of therapy as phenylbutyrate is far more expensive than benzoate (Cederbaum et al., 2010). A direct comparison between the medications as well as exploring the utility of combinatorial therapy with both medications would be of value in devising cost-effective management strategies for UCDs.

The present disclosure provides a solution to a long-felt need for effective treatment for UCDs.

BRIEF SUMMARY

Embodiments of the disclosure provide methods and compositions for the treatment of one or more UCDs and/or for prevention of hyperammonemia in one or more UCDs. In particular embodiments, the methods and compositions encompass compositions for treating UCDs that have more than one compound, and the multiple compounds may or may not act synergistically or may or may not act additively, including in vivo. The compositions may comprise, consist of, or consist essentially of phenylbutyric acid or a pharmaceutically acceptable salt or prodrug thereof (e.g., sodium phenylbutyrate or glycerol phenylbutyrate) and benzoic acid or a pharmaceutically acceptable salt or prodrug thereof (e.g., sodium benzoate), in specific embodiments. In certain embodiments, the amount of sodium phenylbutyrate and sodium benzoate in a composition is of a certain amount, such as no more than a certain level, such as 200 mg/kg/day each.

In one embodiment, there is a method of treating an individual for one or more urea cycle disorders, comprising: administering a therapeutically effective amount of sodium benzoate and sodium phenylbutyrate or glycerol phenylbutyrate, wherein, the sodium benzoate and sodium phenylbutyrate or glycerol phenylbutyrate are each administered at no more than 200 mg/kg/day. The urea cycle disorder may encompass one or more of the following diseases: N-acetylglutamate synthase deficiency (NAGS deficiency), Carbamoyl-phosphate synthase 1 deficiency (CPS1 deficiency), Ornithine transcarbamylase deficiency (OTC deficiency), Ornithine translocase (ORNT1) deficiency, Citrullinemia type I (ASS1 deficiency), Argininosuccinic aciduria (ASL deficiency), Arginase deficiency (hyperargininemia, ARG1 deficiency), and/or Citrin deficiency.

In some cases, the sodium benzoate and sodium phenylbutyrate or glycerol phenylbutyrate is administered to the individual orally. The sodium benzoate and sodium phenylbutyrate or glycerol phenylbutyrate may be administered to the individual daily, weekly, multiple times in a week, bi-weekly, or monthly and/or may be administered to the individual with or without food and/or drink. In specific cases, the sodium benzoate is administered in a dosage of 20-200 mg/kg/day and/or the sodium phenylbutyrate or glycerol phenylbutyrate is administered in a dosage of 20-200 mg/kg/day. The amount of sodium phenylbutyrate or glycerol phenylbutyrate administered may be greater on a mole:mole basis than the amount of sodium benzoate administered.

The sodium benzoate and sodium phenylbutyrate or glycerol phenylbutyrate may be administered as a single composition comprising both sodium benzoate and sodium phenylbutyrate. The sodium benzoate and sodium phenylbutyrate or glycerol phenylbutyrate may be administered as separate compositions. In specific embodiments, the ratio of sodium phenylbutyrate or glycerol phenylbutyrate to sodium benzoate in the composition is 1:1 or greater on a mole:mole basis. The amount of sodium phenylbutyrate or glycerol phenylbutyrate administered may be less on a mole:mole basis than the amount of sodium benzoate administered. The ratio of sodium phenylbutyrate or glycerol phenylbutyrate to sodium benzoate in the composition may be 1:1 or less on a mole:mole basis, in specific embodiments.

In some embodiments, there is a method of treating an individual with a medical disorder or drug side effect associated with nitrogen retention, comprising: administering a therapeutically effective amount of sodium benzoate and sodium phenylbutyrate or glycerol phenylbutyrate, wherein, the sodium benzoate and sodium phenylbutyrate or glycerol phenylbutyrate are each administered at no more than 200 mg/kg/day. The disorder in the individual may comprise hepatic encephalopathy (HE), metabolic disorders, vascular bypass of the liver, biliary atresia, and/or acute liver failure. In certain embodiments, the drug associated with nitrogen retention in the individual is valproic acid, cyclophosphamide, and/or 5-pentanoic acid. The individual may be treated with an additional drug or therapy, such as one that comprises PAA precursors, supplementation of a deficient amino acid, carbamyl glutamate, and/or arginine hydrochloride. The deficient amino acid may be arginine and/or citrulline. In certain embodiments, the therapy comprises pump-driven extra corporeal membrane oxygenation (ECMO) hemodialysis, intermittent hemofiltration, intermittent hemodialysis, continuous renal replacement therapy, and/or peritoneal dialysis. A disorder in the individual may be identified by family history, physical examination, biochemical assay (for example, one that comprises plasma ammonia concentration determination, quantitative plasma amino acid analysis (of citrulline, arginine, and/or ornithine), urinary orotic acid concentration determination, and/or urine amino acid analysis), and/or molecular genetic testing (serial single-gene testing, a multi-gene panel, exome sequencing and/or genome sequencing, for example).

In one embodiment, there is a method of treating an individual for one or more urea cycle disorders, comprising: administering a therapeutically effective amount of sodium benzoate and sodium phenylbutyrate, wherein, the sodium benzoate and sodium phenylbutyrate are each administered at no more than 400 mg/kg/day.

In a certain embodiment, there is a composition comprising sodium benzoate and sodium phenylbutyrate or glycerol phenylbutyrate. The amount of sodium benzoate and sodium phenylbutyrate or glycerol phenylbutyrate may be each at least 2 g. The composition may be a solid, liquid, or gel. The composition may be in the form of a solution, suspension, emulsion, tablet, pill, capsule, film, sustained release formulation, buccal composition, troche, elixir, syrup, wafer, or combination thereof. In specific cases, the ratio of sodium phenylbutyrate or glycerol phenylbutyrate to sodium benzoate in the composition is 1:1 or greater on a mole:mole basis. The ratio of sodium phenylbutyrate or glycerol phenylbutyrate to sodium benzoate in the composition may be 1:1 or less on a mole:mole basis.

Embodiments of the disclosure include kits that comprise any composition encompassed herein. In specific cases, the kit comprises (a) a composition comprising sodium phenylbutyrate or glycerol phenylbutyrate and (b) a composition comprising sodium benzoate.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawings.

DETAILED DESCRIPTION

Figure 1:
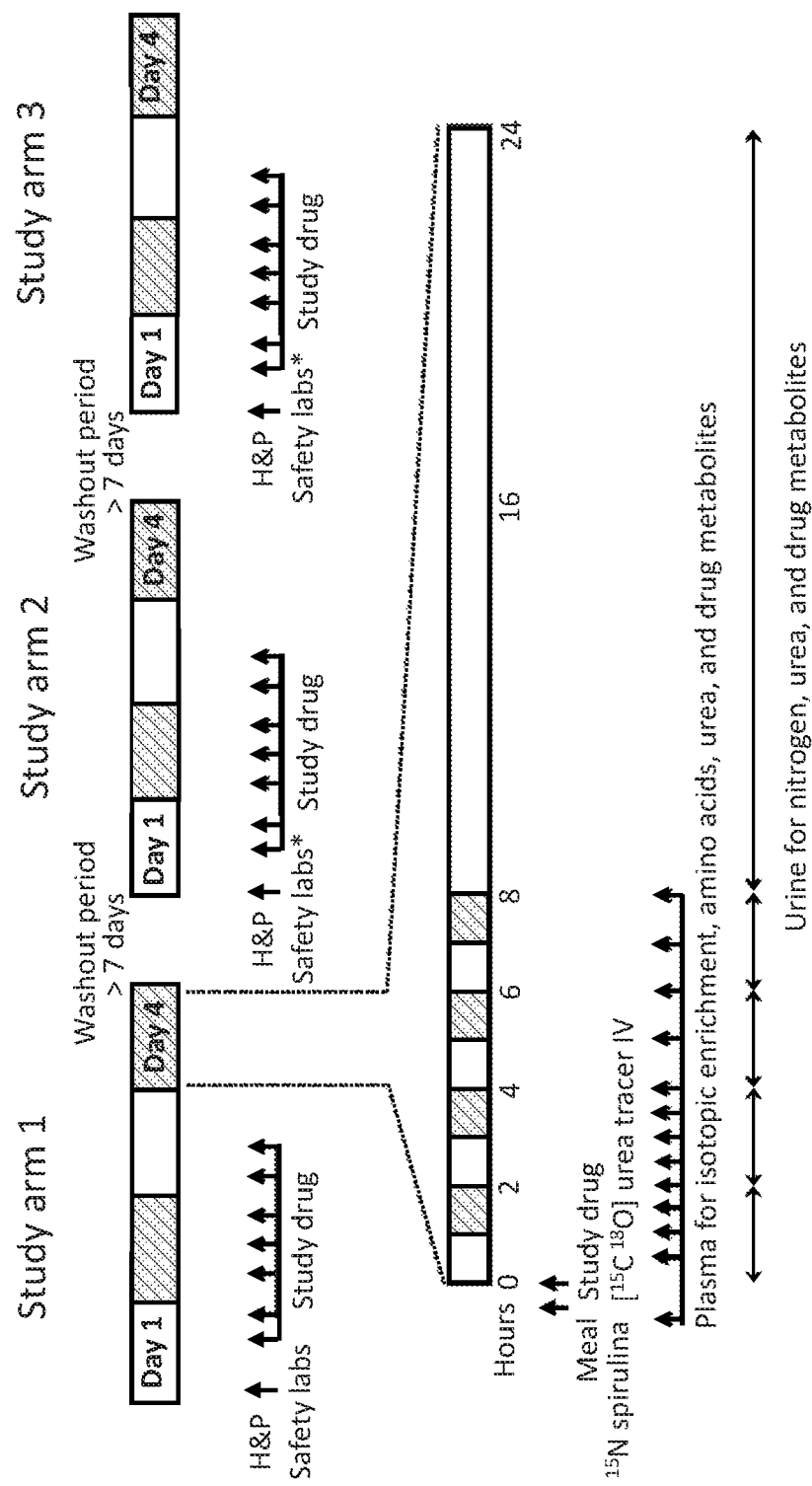
FIG. 1 is a schematic depicting an example of a study design and procedures. Every subject was crossed over to receive all three study medications, i.e., phenylbutyrate, benzoate and combination of phenylbutyrate and benzoate at half the dose. (H&P—history and physical examination; Safety labs—complete blood count, comprehensive metabolic panel, plasma ammonia, and urinalysis; * safety labs in study arms 2 and 3 were repeated only if abnormalities were noted on safety labs from the Day 4 of the preceding study arm or if the washout period was greater than 28 days from the preceding treatment arm)
Figure 2:
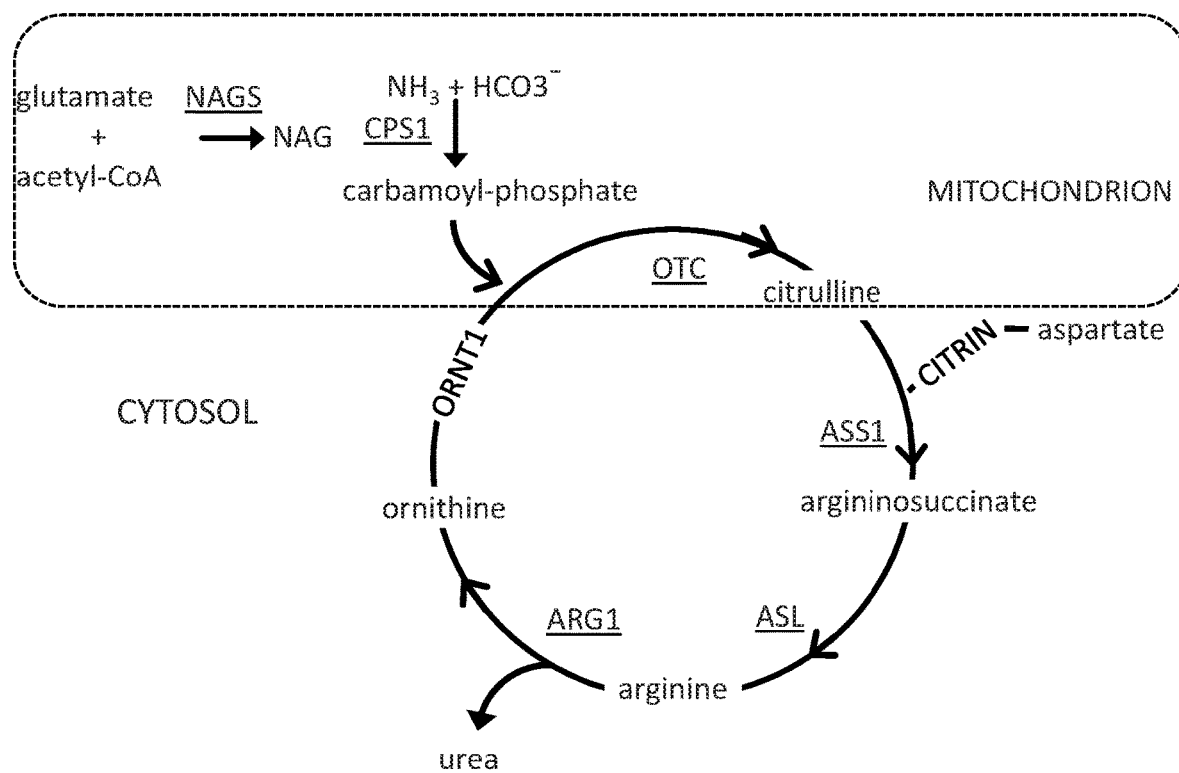
FIG. 2 is a schematic representation of the urea cycle. NAGS—N-acetylglutamate synthase; CPS1—carbamoyl-phosphate synthase 1; OTC—ornithine transcarbamylase; ASS1—argininosuccinate synthase 1; ASL—argininosuccinate lyase; ARG1—arginase 1; Citrin-mitochondrial aspartate/glutamate carrier; ORNT1 mitochondrial ornithine transporter
Figure 3:
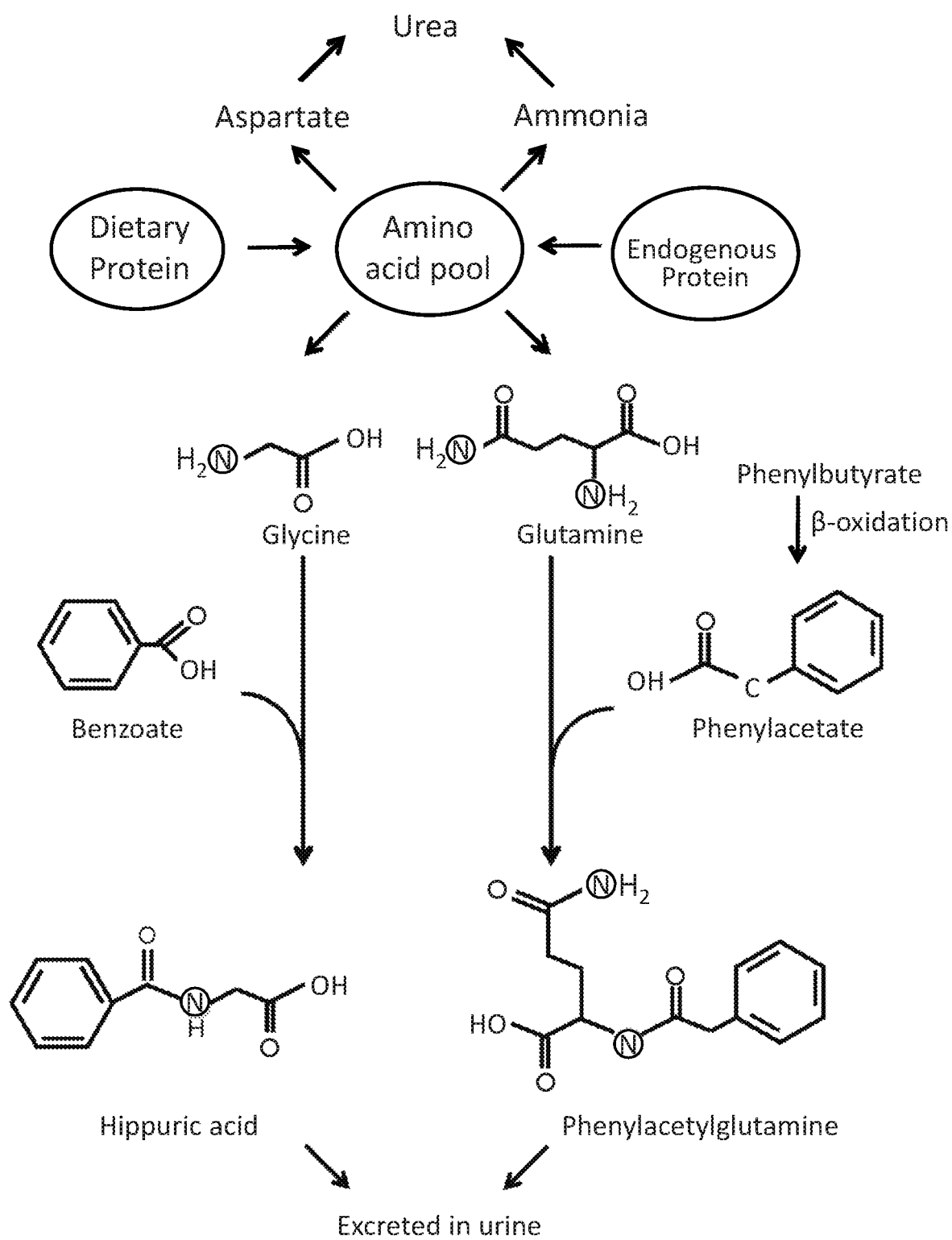
FIG. 3 shows an alternate pathways for nitrogen disposal. With a block in ureagenesis, excretion of conjugates of amino acids can serve as an alternative mechanism for disposal of nitrogen. Benzoate and phenylacetate can be conjugated with glycine and glutamine, respectively to generate hippuric acid and phenylacetylglutamine. The nitrogen atoms scavenged by these medications is depicted by grey circles. Whereas one molecule of benzoate scavenges one atom of nitrogen, one molecule of phenylacetate (or its precursor, phenylbutyrate) scavenges two atoms of nitrogen.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein.

The present disclosure concerns methods and compositions concerning treatment of urea cycle disorders with combination therapy that employs at least benzoic acid or a pharmaceutically acceptable salt or prodrug thereof (e.g., sodium benzoate) and/or at least phenylbutyric acid or a pharmaceutically acceptable salt or prodrug thereof (e.g., sodium phenylbutyrate or glycerol phenylbutyrate). The combination therapy utilizes particular concentrations, in at least some respects. In particular embodiments, the combination of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) allows for reduced levels of at least one of the compounds for treatment methods and in the composition.

Alternate pathway therapy with benzoate and phenylbutyrate has become a standard-of-care in the management of urea cycle disorders. Whereas these medications are widely used, to date, detailed pharmacokinetic studies, and efficacy on nitrogen excretion have not been systematically studied. The present disclosure provides a randomized, three arm, cross over study to assess the pharmacokinetics of phenylbutyrate and benzoate, and the comparative efficacy of phenylbutyrate, benzoate, and a combination of the two medications (MIX arm) on nitrogen excretion. With the use of stable isotopes, the effects of the medications on urea production and disposal of nitrogen derived from the diet were assessed. $T_{max}$ was similar for both phenylbutyrate and benzoate (~1.5 h). Tmax for phenylacetylglutamine was greater than hippuric acid (3.7 vs. 2.2 h; P<0.008). The efficacy of conjugation (~65%) was similar for phenylbutyrate and benzoate when given as sole treatments (P=0.59); however, surprisingly, the conjugation efficacy of phenylbutyrate and benzoate was greater with the lower dose administered in the MIX arm as compared to the phenylbutyrate arm (P<0.044) and benzoate arm. Phenylbutyrate and MIX treatments were more effective at conjugating and excreting nitrogen than benzoate. The nitrogen excretion as a drug conjugate was similar between the phenylbutyrate and the MIX arms (30.7 vs. 29.8 mmol/24 h; P=QQ). The use of combinatorial therapy increased the mg of nitrogen excreted per USD from 3.7 with phenylbutyrate to 7.1 for combination of benzoate and phenylbutyrate. There were no differences between the treatment arms with respect to urea production, urinary urea nitrogen excretion, or total nitrogen excretion even though the phenylbutyrate arm would be expected to result in greater levels of total nitrogen excretion than the MIX arm since, as noted above, phenylbutyrate conjugates to glutamine which has two nitrogens while benzoate conjugates to glycine which has only one nitrogen. Accordingly, the MIX arm which includes 50% of the dose of phenylbutyrate in the phenylbutyrate arm and 50% of the dose of benzoate in the benzoate arm would be predicted to result in 75% of the total nitrogen excretion of the phenylbutyrate arm. Phenylbutyrate was more efficacious than benzoate at conjugating and disposing of nitrogen. Combinatorial therapy with phenylbutyrate and benzoate significantly reduces the cost of treatment cost without compromising the amount of nitrogen conjugated. In embodiments of the disclosure, combinatorial therapy with phenylbutyrate and benzoate in urea cycle disorders is useful to reduce the cost of treatment without compromising the nitrogen-excretion capacity as compared to monotherapy with a higher dose of phenylbutyrate.

I. Compositions of the Disclosure

Embodiments of the disclosure include compositions that comprise benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate). The benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) may or may not be formulated in the same composition entity, given that the benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) may or may not be administered to an individual in the same composition. However, in particular embodiments, the benzoic acid or a pharmaceutically acceptable salt or prodrug thereof (e.g., sodium benzoate) and sodium phenylbutyric acid or a pharmaceutically acceptable salt or prodrug thereof (e.g., sodium phenylbutyrate or glycerol phenylbutyrate) are comprised within the same composition.

In specific embodiments, each of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) is administered at no more than 20, 25, 50, 75, 100, 125, 150, 175, 200, 250, 300, 400, 450, 500, 550, or 600 mg/kg/day, and in specific embodiments, the composition comprises, consists of, or consists essentially of each of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) in a range of 20-200, 20-175, 20-150, 20-125, 20-100, 20-75, 20-50, 20-25, 40-200, 40-175, 40-150, 40-125, 40-100, 40-80, 40-75, 40-50, 50-200, 50-175, 50-150, 50-125, 50-100, 50-75, 50-60, 60-200, 60-175, 60-150, 60-125, 60-100, 60-75, 80-200, 80-175, 80-150, 80-125, 80-120, 80-100, 80-90, 100-200, 100-175, 100-150, 100-140, 100-125, 120-200, 120-175, 120-160, 120-150, 140-200, 140-180, 140-175, 140-150, 160-200, 160-175, or 180-200 mg/kg/day per drug, merely as examples. In some embodiments, each of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) is administered in about 1 g to 20 g per day (e.g., 1 to 5 g per day, 2 to 7 g per day, 5 to 10 g per day, 7 to 15 g per day, or 10 to 20 g per day). In alternative embodiments, the composition comprises, consists of, or consists essentially of each of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) at no more than 400 mg/kg/day, and in specific embodiments, the composition comprises, consists of, or consists essentially of each of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) in a range of 20-600 mg/kg/day. The benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) may be in a range of 20-600, 20-300, 20-200, 20-100, 50-400, 50-300, 50-200, 50-100, 100-400, 100-300, 100-200, 200-400, 200-400, 300-500, or 400-600 mg/kg/day, for example. In some embodiments, the benzoic acid or pharmaceutically acceptable salt or prodrug thereof (e.g., sodium benzoate) and/or phenylbutyric acid or pharmaceutically acceptable salt or prodrug thereof (e.g., sodium phenylbutyrate or glycerol phenylbutyrate) may be provided as a dried powder including 1-5 g per teaspoon of active ingredient (e.g., 1-2 g per teaspoon, 1.5-3 g per teaspoon, 2-4 g per teaspoon, or 3-5 g per teaspoon). In some embodiments, the benzoic acid or pharmaceutically acceptable salt or prodrug thereof (e.g., sodium benzoate) and/or phenylbutyric acid or pharmaceutically acceptable salt or prodrug thereof (e.g., sodium phenylbutyrate or glycerol phenylbutyrate) may be provided as a liquid solution or suspension including 0.5-5 g/mL of active ingredient (e.g., 0.5-1.5 g/mL, 1-2 g/mL, 1.5-3 g/mL, 2-4 g/mL, or 3-5 g/mL). In some embodiments, the benzoic acid or pharmaceutically acceptable salt or prodrug thereof (e.g., sodium benzoate) and/or phenylbutyric acid or pharmaceutically acceptable salt or prodrug thereof (e.g., sodium phenylbutyrate or glycerol phenylbutyrate) may be provided as a unit dose for oral consumption, e.g., a tablet, including 50-1000 mg active ingredient (e.g, 50-250 mg, 100-500 mg, 200-750 mg, or 500-1000 mg).

In some aspects of the disclosure, the composition comprises, consists of, or consists essentially of a dose of both benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) that are no less than a certain amount. In specific aspects, the benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) are administered at no less than 150, 160, 170, 175, 180, 185, 190, 195, or 200 mg/kg/day.

Whether or not the phenylbutyric acid or a pharmaceutically acceptable salt or prodrug thereof (e.g., sodium phenylbutyrate or glycerol phenylbutyrate) and the benzoic acid or a pharmaceutically acceptable salt or prodrug thereof (e.g., sodium benzoate) are in the same composition, the amount of phenylbutyric acid or a pharmaceutically acceptable salt or prodrug thereof (e.g., sodium phenylbutyrate or glycerol phenylbutyrate) given to an individual in a dose may or may not be greater than the amount of benzoic acid or a pharmaceutically acceptable salt or prodrug thereof (e.g., sodium benzoate) given to an individual in a dose. In some cases they are equal or substantially equal. When the phenylbutyric acid or pharmaceutically acceptable salt or prodrug thereof (e.g., sodium phenylbutyrate or glycerol phenylbutyrate) and the benzoic acid or pharmaceutically acceptable salt or prodrug thereof (e.g., sodium benzoate) are in separate compositions, they may or may not be administered to an individual at substantially the same time. When provided separately, the phenylbutyric acid or pharmaceutically acceptable salt or prodrug thereof (e.g., sodium phenylbutyrate or glycerol phenylbutyrate) may be given prior to, at the same time as, or subsequent to the benzoic acid or pharmaceutically acceptable salt or prodrug thereof (e.g., sodium benzoate).

As a dosage, including when they are in the same composition, the ratio of phenylbutyric acid or a pharmaceutically acceptable salt or prodrug thereof (e.g., sodium phenylbutyrate or glycerol phenylbutyrate) to benzoic acid or a pharmaceutically acceptable salt or prodrug thereof (e.g., sodium benzoate) may be of any suitable amount. In specific embodiments, the ratio of phenylbutyric acid or a pharmaceutically acceptable salt or prodrug thereof (e.g., sodium phenylbutyrate or glycerol phenylbutyrate) to benzoic acid or a pharmaceutically acceptable salt or prodrug thereof (e.g., sodium benzoate) in the composition is or is about 1:1; 1.25:1; 1.5:1; 1.75:1; 2:1; 2.25:1; 2.5:1; 2.75:1; 3:1; 3.25:1; 3.5:1; 3.75:1; 4:1 (e.g., from 1:1-2:1, 1.5:1-3:1, 2:1-4:1) on a mole:mole basis; and so forth. In some cases, in the composition the amount of phenylbutyric acid or a pharmaceutically acceptable salt or prodrug thereof (e.g., sodium phenylbutyrate or glycerol phenylbutyrate) is less than benzoic acid or a pharmaceutically acceptable salt or prodrug thereof (e.g., sodium benzoate). As examples, a ratio of sodium phenylbutyrate to sodium benzoate is or is about 1:1; 1:1.25; 1:1.5; 1:1.75; 1:2; 1:2.25; 1:2.5; 1:2.75; 1:3; 1:3.25; 1:3.5; 1:3.75; 1:4 or is 1:>4.0 (e.g., from 1:1-1:2, 1:1.5-1:3, 1:2-1:4) on a mole:mole basis.

The composition of phenylbutyric acid or pharmaceutically acceptable salt or prodrug thereof (e.g., sodium phenylbutyrate or glycerol phenylbutyrate) and benzoic acid or pharmaceutically acceptable salt or prodrug thereof (e.g., sodium benzoate) in particular aspects may be in the form of a solid, liquid, or gel at room temperature. The form of the composition may be of any kind, including at least a solution, suspension, emulsion, tablet, pill, capsule, film, sustained release formulation, buccal composition, troche, elixir, syrup, wafer, or combination thereof, for example.

II. Methods of the Disclosure

Methods of the disclosure provide for treatment of one or more UCDs of any kind with a composition(s) that comprises benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate). The concentration of the benzoic acid or pharmaceutically acceptable salt or prodrug thereof (e.g., sodium benzoate) and/or phenylbutyric acid or pharmaceutically acceptable salt or prodrug thereof (e.g., sodium phenylbutyrate or glycerol phenylbutyrate) may be of a specific level in at least some cases. The composition may be administered by a particular route. Any individual of any race or gender or age (infant, child, adolescent, adult) may be treated with methods and compositions of the disclosure but in specific embodiments the individual may be a child.

Any urea cycle disorder may be treated with methods and/or compositions of the disclosure, including N-acetyl-glutamate synthase deficiency (NAGS deficiency), Carbamoyl-phosphate synthase 1 deficiency (CPS1 deficiency), Ornithine transcarbamylase deficiency (OTC deficiency), Ornithine translocase (ORNT1) deficiency, Citrullinemia type I (ASS1 deficiency), Argininosuccinic aciduria (ASL deficiency), Arginase deficiency (hyperargininemia, ARG1 deficiency), or Citrin deficiency, as examples. An individual having a urea cycle disorder may be provided a composition of the disclosure with or without another therapy. The administration may be via any suitable route for the individual, but in specific embodiments the composition is delivered through the alimentary canal, including at least orally or by suppository or by gastrostomy or other forms of enteral feeding devices. By any administration route, the composition may be administered to the individual once or multiple times. When multiple administrations are given to the individual, the frequency may be of any suitable kind, including once a day, more than once a day, once every other day, multiple times a week, once weekly, biweekly, monthly, and so forth. As sodium phenylbutyrate is known to have an unpleasant taste, in some cases, the composition is formulated to enhance patient compliance, for example to have flavoring. The composition(s) may or may not be administered to the individual with or without food and/or drink.

In particular embodiments, a composition comprising benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) are each administered at no more than at no more than 20, 25, 50, 75, 100, 125, 150, 175, 200, 250, 300, 350, 400, 450, 500, 550, or 600 mg/kg/day per drug, and in specific embodiments, the composition is administered to the individual in a range of 20-200, 20-100, 40-80, 60-100, 80-120, 100-140, 120-160, 140-180, 160-200, or 180-200 mg/kg/day per drug, merely as examples. In certain methods, the benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) are administered as urea cycle disorder treatment at no less than 150, 160, 170, 175, 180, 185, 190, 195, or 200 mg/kg/day per drug. In particular clinical embodiments, an individual with a urea cycle disorder is treated with one or more doses of a therapeutically effective combination of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) to improve at least one symptom of the urea cycle disorder. A second or subsequent dose of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) may or may not have the same amount of benzoic acid or a pharmaceutically acceptable salt or prodrug thereof (e.g., sodium benzoate) and/or phenylbutyric acid or a pharmaceutically acceptable salt or prodrug thereof (e.g., sodium phenylbutyrate or glycerol phenylbutyrate) as compared to a previous dose(s).

In some embodiments, there are methods of treating an individual with a medical disorder or drug side effect associated with nitrogen retention (valproic acid, cyclophosphamide, and/or 5-pentanoic acid, for example). The medical disorder may be of any kind, but in specific embodiments the disorder in the individual comprises hepatic encephalopathy (HE), end-stage renal disease (ESRD), cancer, neurodegenerative disorders such as Huntington's Disease, amyotrophic lateral sclerosis (ALS), spinal muscular atrophy (SMA), metabolic disorders, sickle cell disease, herpes simplex virus infection, vascular bypass of the liver, biliary atresia, and/or acute liver failure. Examples of metabolic disorders include maple syrup urine disease (MSUD), phenylketonuria, and/or glutaric acidemia type 1. The individual may or may not be treated with an additional drug or therapy, such as PAA precursors, supplementation of a deficient amino acid (arginine, and/or citrulline, for example), carbamyl glutamate, and/or arginine hydrochloride, for example. The therapy may or may not comprise pump-driven extra corporeal membrane oxygenation (ECMO) hemodialysis, intermittent hemofiltration, intermittent hemodialysis, continuous renal replacement therapy, and/or peritoneal dialysis. In particular embodiments, the disorder in the individual is identified by family history, physical examination, biochemical assays (plasma ammonia concentration determination, quantitative plasma amino acid analysis (of citrulline, arginine, and/or ornithine, for example), urinary orotic acid concentration determination, and/or urine amino acid analysis), and/or molecular genetic testing (for example, that comprises serial single-gene testing, a multi-gene panel, exome sequencing and/or genome sequencing). In specific embodiments, a therapeutically effective amount of the composition(s) is administered through the alimentary canal, and the composition comprises, consists of, or consists essentially of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate). In specific cases, benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) are each administered at no more than 200, 300, 400, 500, or 600 mg/kg/day, and benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) may act synergistically in the individual.

Dietary management, such as protein restriction, may be part of the individual's treatment. Oral lactulose, Neosporin, multivitamins, calcium and/or antioxidant supplements may additionally or alternatively be employed.

In some embodiments, methods of the disclosure encompass methods of preventing one or more urea cycle disorders, such as preventing the occurrence of one or more urea cycle disorders, delaying the onset of one or more urea cycle disorders, reducing the severity of one or more urea cycle disorders, and so forth. In some cases, the composition(s) of the disclosure is provided to an individual at risk for one or more urea cycle disorders, such as an individual tested positive for a genetic predisposition to one or more urea cycle disorders, a family history of one or more urea cycle disorders (for example, present in an older sibling), and so forth.

III. Pharmaceutical Preparations

Pharmaceutical compositions of the present disclosure comprise an effective amount of one or more compositions comprising, consisting of, or consisting essentially of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one composition comprising, consisting of, or consisting essentially of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) will be known to those of skill in the art in light of the present disclosure, as exemplified by Remington (Remington: The Science and Practice of Pharmacy, (22nd ed.) ed. L. V. Allen, Jr., 2013, Pharmaceutical Press, Philadelphia, Pa.) incorporated herein by reference. Moreover, for animal (e.g., human, dog, cat, horse, and so forth) administration, it will be understood that preparations may meet sterility, pyrogenicity, general safety and purity standards as required by FDA Office of Biological Standards or another regulatory agency.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition comprising, consisting of, or consisting essentially of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) (or the separate compositions of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate)) may comprise different types of carriers depending on whether it is to be administered in solid, liquid or aerosol form, and whether it need to be sterile for such routes of administration as injection. The presently disclosed compositions may be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington).

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition(s) and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The composition(s) may be formulated into a composition in a neutral or salt form. Pharmaceutically acceptable salts, include salts derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the comprising, consisting of, or consisting essentially of benzoic acid or a pharmaceutically acceptable salt or prodrug thereof (e.g., sodium benzoate) and phenylbutyric acid or a pharmaceutically acceptable salt or prodrug thereof (e.g., sodium phenylbutyrate or glycerol phenylbutyrate) is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations that are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin or combinations thereof.

IV. Kits

Any of the compositions described herein may be comprised in a kit. In a non-limiting example, a composition comprising, consisting of, or consisting essentially of sodium benzoate and sodium phenylbutyrate (or separate compositions of sodium benzoate and sodium phenylbutyrate) may be comprised in a kit. The kits will thus comprise, in suitable container means, one or more composition(s). In some embodiments, the kit includes (a) a composition including phenylbutyric acid or a pharmaceutically acceptable salt or prodrug thereof (e.g., sodium phenylbutyrate or glycerol butyrate) and (b) a composition including benzoic acid or a pharmaceutically acceptable salt or prodrug thereof (e.g., sodium benzoate).

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the composition and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. In some embodiments, the kit includes at least two containers, one container including phenylbutyric acid or a pharmaceutically acceptable salt or prodrug thereof (e.g., sodium phenylbutyrate or glycerol butyrate) as a liquid solution and one container including benzoic acid or a pharmaceutically acceptable salt or prodrug thereof (e.g., sodium benzoate) as a liquid solution. In some embodiments, the kit includes at least two containers, one container including phenylbutyric acid or a pharmaceutically acceptable salt or prodrug thereof (e.g., sodium phenylbutyrate or glycerol butyrate) as a liquid solution and one container including benzoic acid or a pharmaceutically acceptable salt or prodrug thereof (e.g., sodium benzoate) as a dried powder.

However, the components of the kit may be provided as dried powder(s). When reagents and/or components are provided as a dry powder, the powder can be reconstituted by the addition of a suitable solvent. It is envisioned that the solvent may also be provided in another container means. In some embodiments, the kit includes at least two containers, one container including phenylbutyric acid or a pharmaceutically acceptable salt or prodrug thereof (e.g., sodium phenylbutyrate or glycerol butyrate) as a dried powder and one container including benzoic acid or a pharmaceutically acceptable salt or prodrug thereof (e.g., sodium benzoate) as a dried powder.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Examples of Materials and Methods

Informed consent was obtained from all participants. Healthy adult volunteers (age ≥18 years) were recruited. Individuals with the following were excluded from the study: 1) history of dietary protein intolerance, 2) history of liver diseases, 3) inability to follow the prescribed diet or undergo the isotopic infusions, 4) documented history of hyperammonemia (defined as plasma ammonia >100 μmol/L), 5) clinical or laboratory abnormality of Grade 3 or greater according to the Common Terminology Criteria for Adverse Events v.4.0 (CTCAE), and 6) any condition(s) not covered by the CTCAE, but in the opinion of investigators, constituted a severe condition. Pregnant or lactating women were not enrolled.

Study Design

This was a randomized, three-arm, crossover study. Each arm was completed over a four-day period with a washout period of at least 7 days between any two of the treatment arms (FIG. 1). The treatment sequence was randomized in a non-blinded manner. The treatment and doses of the medications used were as follows: 1) NaPB arm: phenylbutyrate 7.15 $g \cdot m^{-2}$ of body surface area $(BSA) \cdot day^{-1}$; maximum dose, 20 $g \cdot day^{-1}$, 2) NaBz arm: benzoate 5.5 $g \cdot m^{-2}$ of $BSA \cdot day^{-1}$; maximum dose, 12 $g \cdot day^{-1}$, and 3) MIX arm: phenylbutyrate and benzoate, 3.575 and 2.75 $g \cdot m^{-2}$ of $BSA \cdot day^{-1}$, respectively (half the dose used in the NaPB and NaBz arms). The treatments were designed to provide isomolar amount of drugs and the total daily dose was administered in three equally divided doses. The doses of medications used in the study is representative of the typical doses that are used in the management of adult UCDs (Haberle et al., 2012).

On day 1 of study arm 1, detailed medical history review and physical examination were performed. Complete blood count, comprehensive metabolic panel, plasma ammonia, and urinalysis (safety laboratory measurements) were performed. Urine pregnancy test was performed on all females. Meals prepared at the CNRC to provide 0.8 $g \cdot kg^{-1} \cdot day^{-1}$ protein and 32 $kcal \cdot kg^{-1} \cdot day^{-1}$ were given for next three days. The standardized protein and caloric intake allowed for comparison of nitrogen excretion among the three arms. Subjects were randomized to a predetermined treatment sequence and the first dose of the appropriate medication was administered under supervision. Subjects took the study medication with meals for three days (08:00 breakfast; 13:00 lunch; 19:00 dinner) (FIG. 1). Treatment period of three days was chosen to allow for metabolic adaptations to the study medication as we have previously shown, at least for phenylbutyrate, that pharmacokinetics differ when individuals have been on treatment with drug for 3 days as compared to a single dose in naïve subjects (Darmaun et al., 1998; Marini et al., 2011b). On day 3, subjects omitted the 19:00 dose of the medication to prevent interference with the analysis on day 4 from metabolite conjugates from the previous day. On day 4, fasting blood sample was obtained for the determination of plasma amino acids and urea concentrations, background isotopic enrichments, basic metabolic profile, complete blood count, and plasma concentrations of phenylbutyrate, benzoate, PAGN, and HA. Urine was collected for measurements of urea, phenylbutyrate, benzoate, PAGN, and HA. At 0 hours, the test meal containing half of the daily dietary allowance of protein (0.4 $g \cdot kg^{-1}$) was provided by a commercial liquid meal replacement (Ensure Plus, Abbott, Abbot Park, Ill.) and $^{15}N$ labeled spirulina (40 $mg \cdot kg^{-1}$; ISOTEC, Miamisburg, Ohio). Spirulina is a natural source of protein from cyanobacteria that contains ~50% true protein and all essential amino acids (Becker, 2007). A dose of 40 $mg \cdot kg^{-1}$ labeled $^{15}N$-labeled spirulina was estimated to result in dietary enrichment of ~5 mole percent excess. The morning meal, which was ingested in ~10 minutes, was followed by a dose of study medication and an intravenous bolus dose of urea tracer, $[^{13}C^{18}O]$urea (6 mmol/subject; ISOTEC, Miamisburg, Ohio). Blood samples to determine concentrations and isotopic enrichments of the drugs and their conjugated products, as well as amino acids and urea were collected every 30 minutes for the first four hours and then hourly between hours 4 and 8 (FIG. 1). Urine was collected in four 2-hour batched periods during the eight hour admission period. The subjects were then discharged; the urine collection continued at home for the next 16 hours for a total 24 h collection period. The procedures for the study arms 2 and 3 were identical to those performed in arm 1.

Sample Analysis

Plasma and urinary drugs and their conjugated products as well as urea and amino acids were determined by mass spectrometry and quantitated based on the dilution of labeled internal standards. Total urinary nitrogen was determined using the micro-Kjeldahl method.

Plasma and urinary phenylbutyrate, PAA, and benzoate were determined as their pentafluorobenzyl derivatives by NCI-GC-MS; Rid Benzoic (99.2% D) and [$^2H_{11}$] 4-phenylbutyric acids (C/D/N Isotopes, Quebec, Canada) were used as internal standards. Underivatized PAGN and HA were measured by HESI LC-MS/MS; [$^2H_5$] PAGN and [$^2H_5$] HA (C/D/N Isotopes, Quebec, Canada) were used as internal standards.

Plasma amino acids concentrations and enrichments were determined by HESI LC-MS/MS. A cell free U-[$^{13}C^{15}N$] amino acid mix was used as internal standard. Total urinary nitrogen was determined using the micro-Kjeldahl method.

Urea enrichment and concentration in plasma and urine were measured using EI GC-MS as previously published (Beylot et al., 1994).

Calculations

Pharmacokinetic parameters, time to peak concentration of the drugs and their conjugated products (Tmax), peak concentration (Cmax), and area under the curve for 8 h after drugs ingestion ($AUC_{0-8}$) were determined using previously published methodology (Urso et al., 2002). Urea production was determined by non-compartmental analysis after fitting a biexponential model to the [$^{13}C^{18}O$] urea enrichment data (Matthews and Downey, 1984; Marini et al., 2006).

The total amount of nitrogen conjugated by drugs was calculated by multiplying the weight of 24 h urine, the concentration of the metabolite of interest, and the nitrogen content of the metabolite. PAGN and HA were detected in the urine of subjects during treatment arms in which they were not receiving phenylbutyrate or benzoate, respectively. Accordingly, these background values were subtracted from the values obtained during the treatment with phenylbutyrate and benzoate. The total amount of nitrogen conjugated was expressed as fraction of the test meal, by dividing by the total nitrogen content of the test meal. The conjugation of dietary nitrogen was calculated as the amount of $^{15}N$ conjugated by multiplying the total amount of nitrogen conjugated by the respective $^{15}N$ enrichment. For PAGN, the labeling of the amino and amido group were considered.

Efficacy of drug conjugation, the technical relationship between the drug and its effects (Mackenzie and Dixon, 1995), was determined by dividing the amount of nitrogen conjugated by the amount of drug provided (in a molar and gram basis).

Statistical Analysis

Data were analyzed using the proc mixed procedure of SAS (v. 9.4; SAS Institute, Cary, N.C.) with subject as the random variable; thus comparisons were done within subject. If statistically significant effect for a particular treatment arm was observed (P<0.05), post hoc Tukey procedure was performed for multiple pairwise comparisons. Data are expressed as means±SEM.

Example 2

Comparing Efficacy of Phenylbutyrate and Benzoate on Nitrogen Excretion nd Ureagenesis In Healthy Volunteers Results Seven individuals (5 males, 2 females) were enrolled. The demographic characteristics and the treatment sequences are outlined in Table 1A.

TABLE 1A

Subjects enrolled in the trial and treatment sequence

| Subject | Age in yrs. | Sex | Ht in cm | Wt in kg | BSA in m² | Treatment sequence |
|---|---|---|---|---|---|---|
| 1 | 52 | M | 177.1 | 76.2 | 1.933 | NaPB → MIX → NaBz |
| 2 | 28 | M | 177.4 | 74.5 | 1.917 | MIX → NaBz → NaPB |
| 3 | 26 | M | 171.4 | 65.2 | 1.766 | NaPB → MIX → NaBz |
| 4 | 58 | M | 188.8 | 93.2 | 2.205 | NaBz → MIX → NaPB |
| 5 | 33 | F | 163.5 | 59.5 | 1.642 | MIX → NaPB → NaBz |
| 6 | 27 | M | 171.3 | 74.5 | 1.869 | NaBz → MIX → NaPB |
| 7 | 23 | F | 161.7 | 93.5 | 1.974 | NaPB → MIX → NaBz |

NaPB—phenylbutyrate arm; NaBz—benzoate arm; MIX—combination of phenylbutyrate and benzoate Pharmacokinetics of Phenylbutyrate, Benzoate, and their Conjugated Products After a 3-day treatment adaptation, pharmacokinetics were determined following a single drug dose on day 4 (Table 1B, FIG.). Tmax for phenylbutyrate and benzoate were not different whether the drugs were given alone or in combination (P>0.28). Tmax for PAA was greater than Tmax for phenylbutyrate (P<0.001), and tended to be greater in the NaPB arm as compared to the MIX arm (P=0.086). As expected, Cmax and $AUC_{0-8}$ were greater when the drugs were given alone as compared to half the dose in the MIX arm. Phenylbutyrate and PAA Cmax and $AUC_{0-8}$ were ~2-3 times greater when subjects were on the NaPB arm than on the MIX arm. Benzoate Cmax and $AUC_{0-8}$ were ~4-5 times greater when subjects were on the NaBz arm than on the MIX arm.

Figure 4:
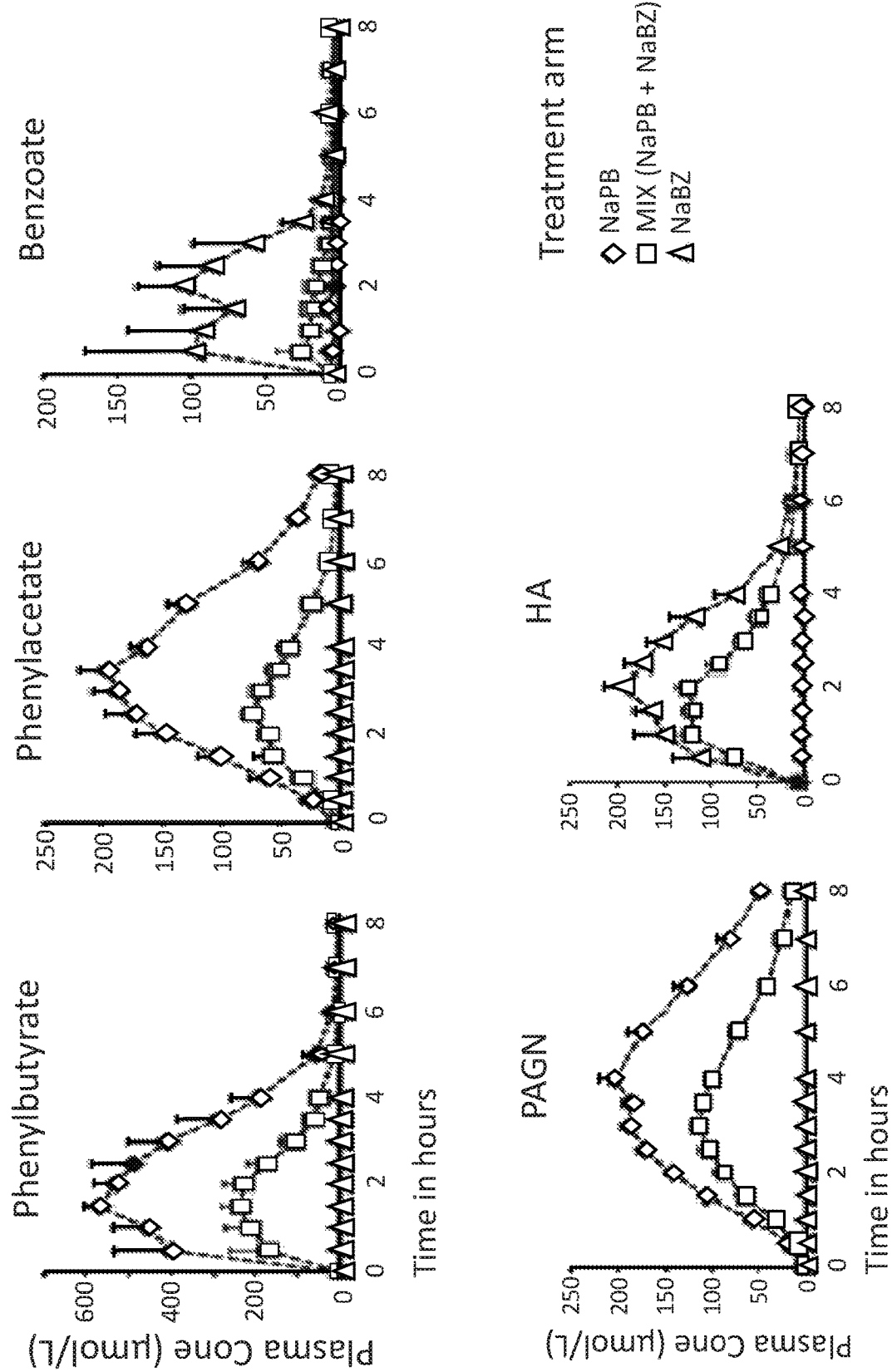
FIG. 4 shows plasma concentrations of phenylbutyrate, benzoate, and their conjugation products. Mean levels and standard errors of mean are depicted.

For the conjugation products, Tmax for PAGN was greater than for HA (P<0.01). For PAGN, no difference in Tmax was observed between the NaPB and MIX arms (P=0.104); however, hippurate Tmax was greater on the NaBz arm than in the MIX arm (P<0.008). As expected, Cmax and $AUC_{0-8}$ for PAGN and HA were greater when phenylbutyrate and benzoate were given solely in the NaPB and NaBz arms as compared to the MIX arm (P<0.014) (Table 1B, FIG. 4). A similar pattern was detected for the conjugation of the drugs with $^{15}N$ labeled glutamine and glycine resulting from the ingestion of the $^{15}N$ labeled test meal.

TABLE 1B

Pharmacokinetics of phenylbutyrate, benzoate, and their conjugated products

| PK/PD parameters Drugs | NaPB arm | MIX arm | NaBz arm | P< |
|---|---|---|---|---|
| PB | | | | |
| Cmax (μmol/L) | 726.8 (61.3) | 333.5 (75.8) | | 0.001 |
| Tmax (h) | 1.5$^b$ (0.4) | 1.5$^b$ (0.2) | | 1.0 |
| AUC$_{0-8}$ (μmol/L) | 1802.6 (215.9) | 662.1 (105.3) | | 0.001 |
| PAA | | | | |
| Cmax (μmol/L) | 211 (18) | 83.3 (10.8) | | 0.001 |
| Tmax (h) | 3.2$^a$ (0.3) | 2.7$^a$ (0.3) | | 0.086 |
| AUC$_{0-8}$ (μmol/L) | 817.7 (83) | 248.9 (37.9) | | 0.001 |
| Bz | | | | |
| Cmax (μmol/L) | | 39.7 (14.4) | 217.2 (65.1) | 0.016 |
| PB | | | | |
| Tmax (h) | | 1.4$^b$ (0.2) | 1.6$^b$ (0.4) | 0.28 |
| AUC$_{0-8}$ (μmol/L) | | 72.9 (9.6) | 301.7 (77.8) | 0.021 |
| Conjugated Products | | | | |
| PAGN | | | | |
| Cmax (μmol/L) | 207.9 (15.6) | 120.6 (10.4) | | 0.001 |
| Tmax (h) | 3.7$^a$ (0.2) | 3.2$^a$ (0.2) | | 0.104 |
| AUC$_{0-8}$ (μmol/L) | 1004.4 (71.7) | 489.5 (36) | | 0.001 |
| HA | | | | |
| Cmax (μmol/L) | | 155 (20.2) | 218 (23.4) | 0.014 |
| Tmax (h) | | 1.5$^b$ (0.2) | 2.2$^b$ (0.3) | 0.008 |
| AUC$_{0-8}$ (μmol/L) | | 392.3 (35.6) | 641.2 (70.3) | 0.002 |
| Conjugated $^{15}$N Products | | | | |
| 2-[$^{15}$N] PAGN | | | | |
| Cmax (μmol/L) | 1.44 (0.35) | 0.88 (0.22) | | 0.010 |
| Tmax (h) | 3.93$^a$ (0.07) | 3.86$^a$ (0.21) | | 0.76 |
| AUC$_{0-8}$ (μmol/L) | 5.59 (1.78) | 3.25 (0.87) | | 0.061 |
| 5-[$^{15}$N] PAGN | | | | |
| Cmax (μmol/L) | 2.95 (0.71) | 1.93 (0.44) | | 0.026 |
| Tmax (h) | 4.07$^a$ (0.28) | 3.50$^a$ (0.31) | | 0.066 |
| AUC$_{0-8}$ (μmol/L) | 12.30 (3.08) | 6.95 (1.69) | | 0.015 |
| 2&5-[$^{15}$N] PAGN | | | | |
| Cmax (μmol/L) | 0.67 (0.09) | 0.46 (0.07) | | 0.060 |
| Tmax (h) | 3.64$^a$ (0.14) | 3.14$^a$ (0.39) | | 0.234 |
| AUC$_{0-8}$ (μmol/L) | 2.75 (0.38) | 1.52 (0.20) | | 0.006 |
| [$^{15}$N] HA | | | | |
| Cmax (μmol/L) | | 2.48 (0.49) | 3.12 (0.43) | 0.026 |
| Tmax (h) | | 1.71$^b$ (0.24) | 2.29$^b$ (0.31) | 0.047 |
| AUC$_{0-8}$ (μmol/L) | | 5.82 (0.88) | 8.27 (1.11) | 0.002 |

Figure 5:
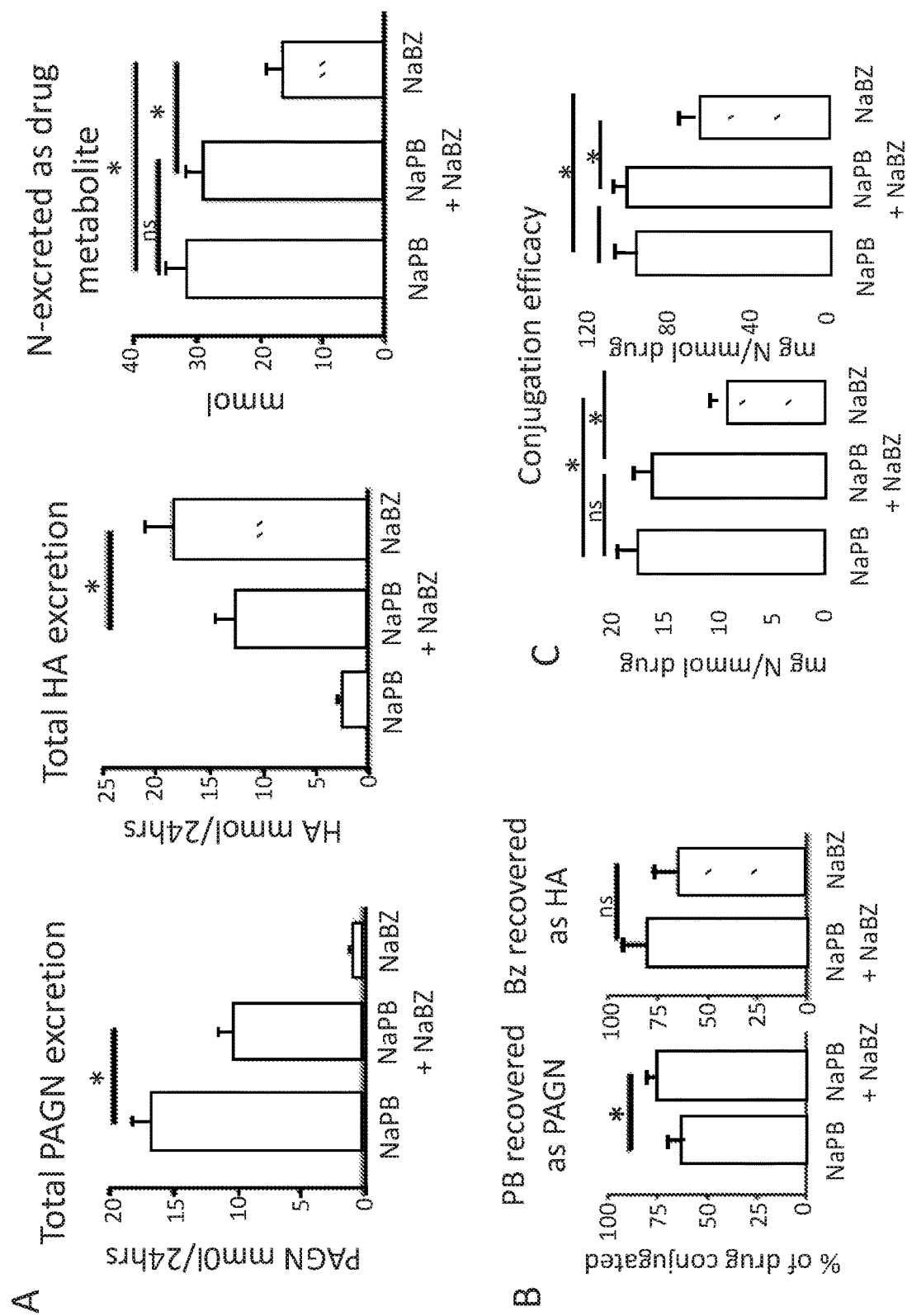
FIGS. 5A-5C show nitrogen excretion as a drug conjugate. 5A Conjugation products of phenylbutyrate (PAGN) and benzoate (HA) excretion in 24 hours. Note that total nitrogen excreted as a drug conjugate in NaPB and the MIX (NaPB+NaBZ) arms is greater than in the NaBZ arm; however, there is no difference between the NaPB and the MIX arms. 5B. The percent of phenylbutyrate recovered as the conjugate product was more when a lower dose was used in the MIX arm compared to NaPB arm. Similar trends are apparent for conversion of benzoate into HA. 5C. The conjugation efficacy, i.e., mg of nitrogen excreted per unit of drug used was higher in the NAPB and MIX arms as compared to the NaBZ arm. *P<0.05

Values depict mean and (standard error of the mean). PK/PD—pharmacokinetic/pharmacodynamics; Cmax—maximal plasma concentration; Tmax—Time to achieve Cmax; AUC$_{0-8}$—area under the curve from time 0 (predose) to 8 h; PB—phenylbutyrate; PAA-phenylacetate; Bz—benzoate; PAGN—phenylacetyglutamine; HA—hippuric acid
$^a$Values with within a section differ P < 0.05
Phenylbutyrate vs bz and conjugates Tmax Urinary Excretion of Phenylbutyrate, Benzoate, and Their Conjugated Products The urinary excretion of phenylbutyrate, PAA, and benzoate were negligible (Table 2). Urine contained an average of 0.8 mmol/d of PAGN and 2.1 mmol/d of HA even when phenylbutyrate and benzoate, respectively, were not administered. After adjusting for these background values, the efficacy of conjugation, i.e., percent of phenylbutyrate dose recovered as PAGN and percent of benzoate dose recovered as HA in 24 h urine were determined. The efficacy of conjugation (~65%) was similar for phenylbutyrate and benzoate when given as the sole treatments (P=0.59); however conjugation efficacy of phenylbutyrate was greater with the lower dose administered in the MIX arm as compared to the NaPB arm (P<0.044). Similar trend was observed for benzoate (P=0.058). A treatment effect (P<0.004) was observed for the total amount of nitrogen excreted as conjugated products. NaPB and MIX treatments were more effective at conjugating and excreting nitrogen than the NaBZ treatment (Table 2; FIG. 5). The efficacy of nitrogen conjugation and excretion was greater for the NaPB and MIX arms as compared to NaBZ arm regardless of whether it was expressed on a per molar (P<0.004) or per gram basis (P=0.032) (Table 2; FIG. 5). However, nitrogen excretion as a drug conjugate was similar between the NaPB and the MIX arms alluding to the fact that combinatorial therapy may be as effective as therapy with NaPB. This is surprising since on a molar basis the MIX arm would be expected to result in only 75% of the nitrogen excretion of the NaPB arm because NaPB conjugates glutamine which has two nitrogen atoms while benzoate conjugates glycine which only has one nitrogen. Further, from a resource utilization standpoint, this would cut the cost of therapy in half. With estimated average costs of phenylbutyrate (USD 24.7/g) and benzoate (USD 0.03/g), the use of combinatorial therapy would increase the mg of nitrogen excreted per USD from 3.7 with phenylbutyrate to 7.1 with a combination of benzoate and phenylbutyrate. For benzoate treatment, 2445.4 mg of nitrogen were excreted per USD. Finally, there was no treatment difference (P=0.19) for the excretion of $^{15}N$ in the conjugated products of phenylbutyrate and benzoate.

with a reduction in $AUC_{0-8}$ in response to phenylbutyrate (P<0.001). The ingestion of the $^{15}N$ labeled test meal resulted in the $^{15}N$ enrichment of all plasma amino acids which peaked around 3-4 h (data not shown). Substantial $^{15}N$ amino acid enrichments were still observed 8 h after the test meal (data not shown).

Effect of Phenylbutyrate and Benzoate on Urea Metabolism and Total Urinary Nitrogen Excretion There was no treatment effect on plasma urea concentration (P=0.16) and urea production (P=0.80) in any of the

TABLE 2

Urinary excretion of phenylbutyrate, benzoate, and their conjugated products

| Drugs | NaPB arm | MIX arm | NaBz arm | P< |
|---|---|---|---|---|
| PB | | | | |
| μmol/24 h | 32.3 (6.1) | 4.1 (1.4) | | 0.003 |
| % of dose | 0.13 (0.03) | 0.03 (0.01) | | 0.009 |
| PAA | | | | |
| μmol/24 h | 40.3 (10.5) | 7.9 (1.4) | | 0.014 |
| % of dose | 0.16 (0.04) | 0.06 (0.01) | | 0.017 |
| Bz | | | | |
| μmol/24 h | | 7.2 (0.9) | 6.5 (1.5) | 0.59 |
| % of dose | | 0.06 (0.01) | 0.02 (0.01) | 0.001 |
| Conjugated Products | | | | |
| PAGN | | | | |
| mmol/24 h | 15.3 (2.3) | 9.3 (0.8) | | |
| % of dose | 61.5 (8.5) | 74.4 (5.4) | | 0.044 |
| HA | | | | |
| mmol/24 h | | 10.5 (1.7) | 16.4 (3.1) | 0.033 |
| % of dose | | 83.8 (12.0) | 66.1 (11.6) | 0.058 |
| Total N | | | | |
| mmol/24 h | $30.7^a$ (4.5) | $29.0^a$ (3.3) | $16.4^b$ (3.1) | 0.004 |
| g N/24 h | $0.43^a$ (0.06) | $0.41^a$ (0.05) | $0.23^b$ (0.04) | 0.004 |
| % test meal | $8.74^a$ (1.19) | $8.20^a$ (0.69) | $4.65^b$ (0.79) | 0.004 |
| Conjugated $^{15}N$ Products | | | | |
| 2-[$^{15}N$] PAGN, μmol/24 h | 43.9 (10.2) | 37.1 (7.2) | | 0.59 |
| 5-[$^{15}N$] PAGN, μmol/24 h | 142.0 (22.7) | 101.1 (11.1) | | 0.15 |
| 2&5-[$^{15}N$] PAGN, μmol/24 h | 38.9 (6.2) | 26.7 (4.4) | | 0.063 |
| HA, μmol/24 h | | 164.0 (30.1) | 253.9 (55.7) | 0.060 |
| Total 15N | 0.26 (0.04) | 0.36 (0.06) | 0.25 (0.06) | 0.19 |
| mg N/24 h | 3.95 (0.64) | 5.34 (0.83) | 3.79 (0.84) | 0.19 |
| % test meal | 1.62 (0.27) | 2.14 (0.24) | 1.51 (0.31) | 0.19 |
| Conjugation efficacy | | | | |
| mg N/mmol drug | $17.2^a$ (2.4) | $16.3^a$ (1.6) | $9.25^b$ (1.6) | 0.004 |
| mg N/g drug | $92.5^{ab}$ (12.8) | $98.6^a$ (9.4) | $64.2^b$ (11.3) | 0.032 |
| Conjugation efficiency | $3.7^C$ (0.5) | $7.1^b$ (0.7) | $2445.4^a$ (429.7) | |

For three group comparisons, values without a common superscript within a row differ P < 0.05

Effect of Benzoate and Phenylbutyrate on Plasma Amino Acids

There was no treatment effect (P>0.13) on glutamine and glycine $AUC_{0-8}$. A treatment effect, however, was detected for leucine $AUC_{0-8}$ (P<0.01), with a reduction in response to phenylbutyrate inclusion in the treatment (P=0.032). This was not evident for the other branched chain amino acids and other amino acids analyzed. The exception was tryptophan which showed a strong treatment effect (P<0.001), three treatment arms (Table 3). Likewise, there was no effect of treatment on total nitrogen (P=0.67) or urea-nitrogen excretion (P=0.74). Total urinary nitrogen excretion accounted for ~67% of the dietary nitrogen and urinary urea nitrogen accounted for ~65.5% of the total urinary nitrogen. Similarly, there was no treatment effect on urea $^{15}N$ excretion (P=0.94); on average urea excretion accounted for ~15% of the test meal nitrogen (Table 3).

TABLE 3

Urea metabolism and total urinary nitrogen excretion

| | NaPB | MIX | NaBz | P< |
|---|---|---|---|---|
| N intake, g/d | 9.81 (0.56) | 9.81 (0.56) | 9.81 (0.56) | — |
| PUN, $AUC_{0-8}$ (µmol/L) | 23.6 (2.2) | 26.3 (2.3) | 25.5 (3.1) | 0.16 |
| Urea production, $\mu mol \cdot kg^{-1} \cdot h^{-1}$ | 192 (14) | 200 (15) | 197 (26) | 0.80 |
| Urinary N, g/d | 6.47 (0.54) | 6.81 (0.63) | 6.38 (0.56) | 0.67 |
| % N excreted from daily intake | 65.6 (3.6) | 70.5 (6.5) | 65.1 (4.6) | 0.48 |
| Urinary Urea N, g/d | 4.16 (0.64) | 4.69 (0.69) | 4.20 (0.58) | 0.74 |
| Urea N as a % total urinary N | 63.6 (6.7) | 67.7 (5.6) | 65.1 (5.3) | 0.88 |
| Urinary urea-$^{15}$N, g/d | 37.0 (4.9) | 38.0 (3.8) | 36.3 (5.0) | 0.94 |
| $^{15}$N as % of test meal | 15.2 (2.1) | 15.5 (1.1) | 14.7 (1.8) | 0.93 |

PUN—plasma urinary nitrogen

Significance of Certain Embodiments

In early 1980s, Saul Brusilow and Mark Batshaw made the serendipitous discovery of the utility of benzoate and phenylacetate in eliciting alternative pathways for nitrogen disposal (Brusilow et al., 1979; Brusilow et al., 1980; Batshaw et al., 1982). Currently phenylbutyrate and benzoate are widely used in the long-term management of UCDs. Whereas benzoate is available as a generic compound and is widely used as a food preservative, phenylbutyrate production is more restricted and currently there are no generic forms available in the US. Over the past two decades, nitrogen-scavenging medications have become a standard-of care in the treatment of individuals with UCDs and their use, at least in part, has contributed to the increased survival of patients (Batshaw et al., 2001; Enns, 2010). However, the cost of treatment and access to medications is far from ideal (Cederbaum et al., 2010). In patients who are able to get medications, the increase in number of pills and side effects associated with higher doses of medication and the cost of treatment can affect compliance (Shchelochkov et al., 2016). Thus, understanding the comparative efficacy of nitrogen-scavenging medications and exploring combinatorial therapy would be an important first step in devising effective and affordable treatment regimens for the treatment of UCDs.

In this study, we demonstrate that the efficacy of phenylbutyrate to conjugate and excrete nitrogen was greater than that of benzoate. However, as expected, none of the drugs conjugated completely with their target amino acids and the efficacy of conjugation of drug with its amino acid at the highest dose of each drug was ~65%. Interestingly, the conjugation efficacy was greater when lower doses of phenylbutyrate and benzoate were used in the MIX arm. A likely reason for this observation was the lack of linearity in the pharmacokinetics of the drugs. Under the assumption of first order kinetics, doubling the dose of the drugs should result in a doubling of the Cmax and AUC; however, phenylbutyrate, PAA, and benzoate Cmax and AUC were significantly greater than expected when phenylbutyrate and benzoate were given as sole treatments as compared to half of these doses in the MIX arm. Moreover, as phenylbutyrate and benzoate conjugate different amino acids the greater efficacy of conjugation with the MIX treatment may be due to the availability of substrate amino acids. An important finding from this study is that combination therapy using benzoate and phenylbutyrate could be as effective as a higher dose of phenylbutyrate. Due to its low cost, the inclusion of benzoate in the MIX arm virtually halved the cost per unit of nitrogen conjugated and excreted without reducing the efficacy of the treatment when compared to the NaPB arm.

The influx of dietary amino acids peaks approximately 3-4 h after a meal (Gaudichon et al., 1999; Bos et al., 2003), which agrees with our observation using the $^{15}$N labeled test meal. Because the drugs were provided with the test meal, the greater efficacy of phenylbutyrate may also be due, at least in part, to a closer match between its pharmacokinetics and the kinetics of protein and amino acid digestion, absorption, and metabolism. However, we could not detect differences in the conjugation and excretion of $^{15}$N between the drugs or among the treatments. Comparable to our previous studies in control subjects receiving phenylbutyrate, there was no treatment differences in urea production, $^{15}$N urea nitrogen and total nitrogen urinary excretion (Marini et al., 2011a). Because benzoate is widely present in foods as a preservative, it was not surprising to find HA in the urine of subjects not receiving benzoate. However, PAGN was also present in the urine of subjects not receiving phenylbutyrate. It is likely that endogenous PAA, generated by a minor pathway of phenylalanine disposal, was responsible for the appearance of this metabolite in urine. Regardless, basal levels of these two metabolites need to be considered when determining the efficiency of drug conjugation in future studies.

A limitation of this study is that it was conducted in healthy subjects. A major goal in the management of UCDs is the control of ammonemia (Lee et al., 2015) and thus the effect of these drugs on plasma ammonia concentration is central to their therapeutic function. Due to the fact that ammonemia is well-controlled in healthy subjects, this endpoint was not assessed. Previous studies on phenylbutyrate metabolism were conducted in fasted and drug naïve individuals (Darmaun et al., 1998; Comte et al., 2002) or in metabolically adapted subjects who were fed small frequent meals (Marini et al., 2011a). A strength of the present study is that the drugs were studied after a 3 day adaptation period and in conjunction with a meal, which better represents the clinical scenario in the management of individuals with UCDs. An additional strength of the study was the use of $^{15}$N spirulina to determine the conjugation and excretion of dietary nitrogen, and thus determining for the first time, the fate of exogenous nitrogen when alternative pathways for nitrogen disposal are elicited.

In summary, on a molar basis, phenylbutyrate was more efficacious than benzoate at conjugating and disposing of nitrogen. The inclusion of both drugs resulted in a reduction of treatment cost without compromising the amount of nitrogen conjugated. The differences found in the pharmacokinetics between the two drugs may be utilized to devise cost-effective management strategies that maximize the efficacy of drug conjugation and at the same time increasing the cost-effectiveness of the therapy.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Ah Mew, N. et al. 1993. Urea Cycle Disorders Overview. In: R. A. Pagon et al. (eds.) GeneReviews®, Seattle (Wash).

Batshaw, M. L. et al. 1982. Treatment of inborn errors of urea synthesis: activation of alternative pathways of waste nitrogen synthesis and excretion. The New England journal of medicine 306: 1387-1392.

Batshaw, M. L., R. B. MacArthur, and M. Tuchman. 2001. Alternative pathway therapy for urea cycle disorders: twenty years later. The Journal of pediatrics 138: S46-54; discussion S54-45.

Becker, E. W. 2007. Micro-algae as a source of protein. Biotechnol. Adv. 25: 207-210.

Beylot, M. et al. 1994. Determination of (13C) urea enrichment by gas chromatography/mass spectrometry and gas chromatography/isotope ratio mass spectrometry. Biological mass spectrometry 23: 510-513.

Bos, C. et al. 2003. Postprandial kinetics of dietary amino acids are the main determinant of their metabolism after soy or milk protein ingestion in humans. J. Nutr. 133: 1308-1315.

Brusilow, S., J. Tinker, and M. L. Batshaw. 1980. Amino acid acylation: a mechanism of nitrogen excretion in inborn errors of urea synthesis. Science 207: 659-661.

Brusilow, S. W., and A. L. Horwich. 2009. The Urea Cycle Enzymes in The Online Metabolic and Molecular Bases of Inherited Disease. The McGraw-Hill Companies, New York.

Brusilow, S. W., D. L. Valle, and M. L. Batshaw. 1979. New pathways of nitrogen excretion in inborn errors of urea synthesis. Lancet 2: 452-454.

Cederbaum, S., C. Lemons, and M. L. Batshaw. 2010. Alternative pathway or diversion therapy for urea cycle disorders now and in the future. Molecular genetics and metabolism 100: 219-220.

Comte, B. et al. 2002. Identification of phenylbutyrylglutamine, a new metabolite of phenylbutyrate metabolism in humans. J. Mass Spectrom. 37: 581-590.

Darmaun, D. et al. 1998. Phenylbutyrate-induced glutamine depletion in humans: effect on leucine metabolism. Am J Physiol 274: E801-807.

Enns, G. M. 2010. Nitrogen sparing therapy revisited 2009. Molecular genetics and metabolism 100 Suppl 1: S65-71.

Gaudichon, C. et al. 1999. Net postprandial utilization of [$^{15}$N]-labeled milk protein nitrogen is influenced by diet composition in humans. J. Nutr. 129: 890-895.

Haberle, J. et al. 2012. Suggested guidelines for the diagnosis and management of urea cycle disorders. Orphanet J Rare Dis 7: 32.

James, M. O., R. L. Smith, R. T. Williams, and M. Reidenberg. 1972. The conjugation of phenylacetic acid in man, sub-human primates and some non-primate species. Proc R Soc Lond B Biol Sci 182: 25-35.

Jones, A. R. 1982. Some observations on the urinary excretion of glycine conjugates by laboratory animals. Xenobiotica 12: 387-395.

Lee, B. et al. 2015. Blood ammonia and glutamine as predictors of hyperammonemic crises in patients with urea cycle disorder. Gen. Med. 17: 561-568.

Lee, B. et al. 2010. Phase 2 comparison of a novel ammonia scavenging agent with sodium phenylbutyrate in patients with urea cycle disorders: safety, pharmacokinetics and ammonia control. Molecular genetics and metabolism 100: 221-228.

Mackenzie, R., and A. K. Dixon. 1995. Measuring the effects of imaging: An evaluative framework. Clin. Radiol. 50: 513-518.

Maestri, N. E., D. Clissold, and S. W. Brusilow. 1999. Neonatal onset ornithine transcarbamylase deficiency: A retrospective analysis. The Journal of pediatrics 134: 268-272.

Marini, J. C. et al. 2011a. Phenylbutyrate improves nitrogen disposal via an alternative pathway without eliciting an increase in protein breakdown and catabolism in control and ornithine transcarbamylase-deficient patients. Am. J. Clin. Nutr. 93: 1248-1254.

Marini, J. C., B. Lee, and P. J. Garlick. 2006. In vivo urea kinetic studies in conscious mice. J. Nutr. 136: 202-206.

Matthews, D. E., and R. S. Downey. 1984. Measurement of Urea Kinetics in Humans—a Validation of Stable Isotope Tracer Methods. Am. J. Physiol. 246: E519-E527.

Mitch, W. E., and S. Brusilow. 1982. Benzoate-induced changes in glycine and urea metabolism in patients with chronic renal failure. J Pharmacol Exp Ther 222: 572-575.

Msall, M., M. L. Batshaw, R. Suss, S. W. Brusilow, and E. D. Mellits. 1984. Neurologic outcome in children with inborn errors of urea synthesis. Outcome of urea-cycle enzymopathies. The New England journal of medicine 310: 1500-1505.

Shchelochkov, O. A. et al. 2016. Barriers to drug adherence in the treatment of urea cycle disorders: Assessment of patient, caregiver and provider perspectives. Mol Genet Metab Rep 8: 43-47.

Simell, O., I. Sipila, J. Rajantie, D. L. Valle, and S. W. Brusilow. 1986. Waste nitrogen excretion via amino acid acylation: benzoate and phenylacetate in lysinuric protein intolerance. Pediatric research 20: 1117-1121.

Urso, R., P. Blardi, and G. Giorgi. 2002. A short introduction to pharmacokinetics. Eur. Rev. Med. Pharmacol. Sci. 6: 33-44.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A kit comprising (a) a composition comprising sodium phenylbutyrate or glycerol phenylbutyrate and (b) a composition comprising sodium benzoate, wherein the kit comprises at least two containers, wherein one container comprises sodium phenylbutyrate or glycerol butyrate as a liquid solution and one container comprises sodium benzoate as a liquid solution.

2. A kit comprising (a) a composition comprising sodium phenylbutyrate or glycerol phenylbutyrate and (b) a composition comprising sodium benzoate, wherein the kit comprises at least two containers, wherein one container comprises sodium phenylbutyrate or glycerol butyrate as a liquid solution and one container comprises sodium benzoate as a dried powder.

3. The kit of claim 1, wherein the composition of (a) is a solid, liquid, or gel.

4. The kit of claim 1, wherein the composition of (a) is in the form of a solution, suspension, emulsion, tablet, pill, capsule, sustained release formulation, elixir, syrup, or combination thereof.

5. The kit of claim 1, wherein the ratio of sodium phenylbutyrate or glycerol phenylbutyrate to sodium benzoate in the kit is 1:1 or greater on a mole:mole basis.

6. The kit of claim 1, wherein ratio of sodium phenylbutyrate or glycerol phenylbutyrate to sodium benzoate in the kit is 1:1 or less on a mole:mole basis.

7. The kit of claim 1, wherein the composition of (a) comprises sodium phenylbutyrate, and the sodium phenylbutyrate is in the form of a powder.

8. The kit of claim 2, wherein the composition of (a) is a solid, liquid, or gel.

9. The kit of claim 2, wherein the composition of (a) is in the form of a solution, suspension, emulsion, tablet, pill, capsule, sustained release formulation, elixir, syrup, or combination thereof.

10. The kit of claim 2, wherein the ratio of sodium phenylbutyrate or glycerol phenylbutyrate to sodium benzoate in the kit is 1:1 or greater on a mole:mole basis.

11. The kit of claim 2, wherein the ratio of sodium phenylbutyrate or glycerol phenylbutyrate to sodium benzoate in the kit is 1:1 or less on a mole:mole basis.

12. The kit of claim 2, wherein the composition of (a) comprises sodium phenylbutyrate, and the sodium phenylbutyrate is in the form of a powder.

\* \* \* \* \*